(12) United States Patent
Ahn et al.

(10) Patent No.: US 10,281,418 B2
(45) Date of Patent: May 7, 2019

(54) MICRO HEATER AND MICRO SENSOR

(71) Applicant: Point Engineering Co., Ltd., Asan-si (KR)

(72) Inventors: Bum Mo Ahn, Suwon-si (KR); Seung Ho Park, Hwaseong-si (KR); Sung Hyun Byun, Hwaseong-si (KR)

(73) Assignee: Point Engineering Co., Ltd., Asan-si, Chungcheongnam-do (KR)

( * ) Notice: Subject to any disclaimer, the term of this patent is extended or adjusted under 35 U.S.C. 154(b) by 190 days.

(21) Appl. No.: 15/247,530

(22) Filed: Aug. 25, 2016

(65) Prior Publication Data
US 2017/0067842 A1 Mar. 9, 2017

(30) Foreign Application Priority Data

Sep. 4, 2015 (KR) .................. 10-2015-0125572

(51) Int. Cl.
| | |
|---|---|
| *G01N 27/12* | (2006.01) |
| *G01N 33/00* | (2006.01) |
| *H05B 3/03* | (2006.01) |
| *H05B 3/26* | (2006.01) |

(52) U.S. Cl.
CPC ......... *G01N 27/123* (2013.01); *G01N 27/125* (2013.01); *G01N 27/128* (2013.01); *G01N 33/0027* (2013.01); *H05B 3/03* (2013.01); *H05B 3/265* (2013.01)

(58) Field of Classification Search
None
See application file for complete search history.

(56) References Cited

U.S. PATENT DOCUMENTS

| | | | |
|---|---|---|---|
| 5,464,966 A | 11/1995 | Gaitan et al. | |
| 5,756,971 A | 5/1998 | Hipp | |
| 5,821,402 A | 10/1998 | Okajima et al. | |
| 7,861,575 B2 | 1/2011 | Jun et al. | .......... 73/31.06 |
| 8,325,460 B2 | 12/2012 | Park et al. | .......... 361/286 |
| 8,354,729 B2 | 1/2013 | Hsieh et al. | |
| 10,015,841 B2 | 7/2018 | Ahn et al. | |
| 2002/0104758 A1 | 8/2002 | Mizutani et al. | |
| 2002/0118027 A1 | 8/2002 | Routkevitch et al. | .......... 324/694 |
| 2004/0056016 A1 | 3/2004 | Tian et al. | |

(Continued)

FOREIGN PATENT DOCUMENTS

| | | | | |
|---|---|---|---|---|
| AT | 508 976 A1 | 5/2011 | ............ | G01N 27/12 |
| EP | 2 533 037 A1 | 12/2012 | ............ | G01N 27/12 |

(Continued)

OTHER PUBLICATIONS

Sapphire Aluminum Industries, "Advantages of Anodised Aluminum, Why Use Anodised Aluminum", 2010, pp. 1-2 (captured from Internet Archive—Feb. 18, 2011).*

(Continued)

*Primary Examiner* — Daniel S Larkin
(74) *Attorney, Agent, or Firm* — Sunstein Kann Murphy & Timbers LLP

(57) ABSTRACT

A micro heater includes a heater electrode formed on a first supporting portion. A micro sensor further includes a sensor electrode formed on the first supporting portion. In the micro heater and the micro sensor an anti-etching dam is formed on the supporting portion. The dam protects the shape of the first supporting portion during etching.

13 Claims, 4 Drawing Sheets

(56) References Cited

U.S. PATENT DOCUMENTS

| | | | |
|---|---|---|---|
| 2004/0195096 A1 | 10/2004 | Tsamis et al. | |
| 2004/0213702 A1 | 10/2004 | Ingrisch | |
| 2005/0139993 A1 | 6/2005 | Lee et al. | |
| 2007/0056951 A1 | 3/2007 | Takigawa | |
| 2007/0062812 A1 | 3/2007 | Weber et al. | |
| 2008/0134753 A1 | 6/2008 | Jun et al. | |
| 2009/0151429 A1 | 6/2009 | Jun et al. | |
| 2010/0134948 A1 | 6/2010 | Park et al. | 361/286 |
| 2015/0021716 A1 | 1/2015 | Lee et al. | 257/414 |
| 2015/0285754 A1 | 10/2015 | Park et al. | |
| 2016/0084787 A1 | 3/2016 | Ahn et al. | G01N 27/123 |
| 2016/0370336 A1 | 12/2016 | Ahn et al. | G01N 33/0027 |

FOREIGN PATENT DOCUMENTS

| | | | |
|---|---|---|---|
| JP | 2006-153512 | 6/2006 | G01N 27/22 |
| JP | 2011-149889 A | 8/2011 | |
| JP | 2012-68069 A | 4/2012 | |
| JP | 2012-98232 A | 5/2012 | G01N 25/30 |
| JP | 2012-253082 A | 12/2012 | |
| KR | 10-2009-0061864 | 6/2009 | G01N 1/22 |
| KR | 10-2009-0064693 | 6/2009 | B81C 1/00 |
| KR | 10-2010-0054526 | 5/2010 | G01N 27/12 |
| KR | 10-1019576 | 3/2011 | G01N 27/12 |
| KR | 10-2014-0106082 | 9/2014 | G01N 27/403 |
| KR | 10-2014-0118021 | 10/2014 | G01N 27/407 |
| KR | 2015-0010473 | 1/2015 | G01N 27/12 |
| WO | WO 2009/026592 A1 | 2/2009 | |

OTHER PUBLICATIONS

Korean Intellectual Property Office, Office Action: Notice of Request for Submission of Opinions—Application No. 10-2015-0125572, dated Dec. 16, 2016, 6 pages.

Korean Intellectual Property Office, Office Action: Notice of Request for Submission of Opinions—Application No. 10-2015-0125572, dated Dec. 16, 2016, 6 pages (Machine translation).

Ahn et al., U.S. Appl. No. 15/181,976, filed Jun. 14, 2016, 71 pages.

European Patent Office, Extended European Search Report—Application No. 16186184.4-1554, dated Feb. 3, 2017, 10 pages.

* cited by examiner

MICRO HEATER AND MICRO SENSOR

This application claims the benefit of Korean patent application No. 10-2015-0125572, filed Sep. 4, 2015, the disclosure of which is incorporated herein by reference in its entirety.

BACKGROUND

1. Technical Field

The present invention relates to a micro heater and a micro sensor utilizing anodized film.

2. Description of Related Art

Recently, as the concern about the environment is gradually increasing, there is a need for development of micro sensor capable of acquiring accurate and versatile information in a short period of time. Especially, for comfort control within residential space, management of harmful industrial environment, management of foods and food production processes, and the like, efforts have been progressed in miniaturization, improved precision, and cost reduction of micro sensors, such as a gas sensor, for measuring the relevant gas concentration.

Gas sensors are gradually evolving from the conventional sintered ceramic or thick film structures into micro-electro-mechanical system (MEMS) gas sensors by applying semiconductor process technologies.

In the aspects of measurement method, the most widely used method of gas sensing at this time is measuring the changes in the electrical characteristics when the gas is absorbed by sensing material of the sensor. Generally metal oxides such as $SnO_2$ are used as a sensing material, and the change in the electrical conductivity thereof depending on the concentration of the subject gas is measured, and this method is advantageous in that the measurement is relatively simple. At this time the change in the measurement value is more significant when the metal oxide sensing material is operating at the high temperature. Thus, the precise temperature control is essential for fast and accurate measurement of the gas concentration. In addition, when measuring, the gas concentration is measured after the sensing material is reset to its initial state through high temperature heating, thereby forcibly removing gas species or moisture being already absorbed in the sensing material. Thus, in a gas sensor, the temperature characteristics directly affect major measurement factors such as measurement sensitivity, recovery time, response time, and the like.

Therefore, a type of a micro heater capable of heating only the sensing material portion locally and uniformly is effective for an efficient heating. However, if a large power consumption is required for temperature controlling during the measurement using a micro gas sensor, it requires a large battery or a power source even the volumes of the sensor and the measurement circuit are small, thus, eventually, the overall size of the measurement system will be determined by these factors. Therefore, a structure of low power consumption must be considered first for implementing a micro gas sensor.

Until these days, since silicon substrates having a large thermal conductivity are mostly used when manufacturing most micro sensors, etched pits or grooves are formed inside the sensor structure using a bulk micromachining process so as to reduce heat loss, and then a suspended structure separated from the substrate is formed, and then, on this structure, micro heater, insulating layer, sensing material, and the like are sequentially formed, so that some of heat loss can be reduced. However, in this case, since it is a manufacturing process mainly using a wet etching process utilizing the crystalline directions of the substrate itself, there is a limitation in miniaturization of the sensor device, and there has been a difficulty in compatibility of the properties of etchant like potassium hydroxide (KOH) with the standard CMOS semiconductor process.

And, in FIG. 1 a perspective view of a moisture sensor, which is one of the micro sensors of the prior art, is illustrated.

The moisture sensor 10 comprises a substrate 11, an anodic aluminum oxide (AAO) porous layer 13, and an electrode 15 formed on the anodic aluminum oxide porous layer 13.

The substrate 11 is made of aluminum and formed to be the shape of an approximate rectangular plate. The anodic aluminum oxide porous layer 13 is formed by oxidizing the substrate 11, and when aluminum is being oxidized the anodic aluminum oxide porous layer 13 formed with a plurality holes 13a on the surface thereof can be formed. A barrier layer is formed between the anodic aluminum oxide porous layer 13 and the aluminum.

At this time, the diameter of the hole 13a is formed to be equal or less than 60 nm, so that damages to the hole 13a by the etching solution can be avoided if the diameter of the hole 13a is formed to be equal or less than 60 nm. The electrode 15 comprises metals such as white gold, aluminum, copper, and the like, and it can be formed in various ways such as an evaporation method, and the like.

The electrode 15 comprises a first electrode 16 and a second electrode 17 disposed close to the first electrode 16, wherein an electrode protrusion 16a protruded towards the second electrode 17 is formed in the first electrode 16, and an electrode protrusion 17a protruded towards the first electrode 16 is formed in the second electrode 17.

However, even with the above described structure of the prior art, there is a problem in reducing the heat capacity.

SUMMARY

Technical Problem

The present invention is devised to solve above described problems, and the objective thereof is to provide a micro heater and a micro sensor having a small heat capacity so that the gases to be measured can be quickly and accurately detected with a low power.

Solution to Problem

A micro heater according to the present invention for achieving the above described objectives is characterized in that and comprises: a substrate having a first supporting portion; a heater electrode formed on the first supporting portion; an anti-etching dam formed on the first supporting portion and disposed near the heater electrode; and an air gap formed in the periphery of the first supporting portion.

And, it is characterized in that the anti-etching dam is disposed between the heater electrode and the air gap.

And, it is characterized in that the substrate is an anodized layer wherein the metallic base material is removed after anodizing thereof.

Also, it is characterized in that the air gap is a space formed penetrating from the upper surface of the substrate down towards the bottom surface thereof.

And, it is characterized in that the substrate further comprises a second supporting portion and a bridge portion connecting the first supporting portion and the second supporting portion; and the heater electrode comprises a heating wire formed on the first supporting portion and a heater electrode pad connected to the heating wire and formed on the second supporting portion and the bridged portion.

Also, it is characterized in that the anti-etching dam is formed in the outer side of the heating wire.

And, it is characterized in that the heating wire comprises a plurality of arc portions formed in the shape of an arc, and a plurality of connecting portions connecting the arc portions.

Also, it is characterized in that the air gap is formed in multiple numbers in a discontinuous manner.

And, it is characterized in that the anti-etching dam is made of metal.

A micro sensor according to the present invention for achieving the above described objectives is characterized in that and comprises: a substrate having a first supporting portion; a sensor electrode formed on the first supporting portion; a heater electrode formed on the first supporting portion; an anti-etching dam formed on the first supporting portion and disposed near the heater electrode; and an air gap formed in the periphery of the first supporting portion.

And, it is characterized in that the anti-etching dam is disposed between the heater electrode and the air gap.

And, it is characterized in that the substrate is an anodized layer wherein the metallic base material is removed after anodizing thereof.

Also, it is characterized in that the air gap is a space formed penetrating from the upper surface of the substrate down towards the bottom surface thereof.

And, it is characterized in that the substrate further comprises: a second supporting portion and a bridge portion connecting the first supporting portion and the second supporting portion; the sensor electrode comprises a sensor wire formed on the first supporting portion and a sensor electrode pad connected to the sensor wire and formed on the second supporting portion and the bridged portion; and the heater electrode comprises: a heating wire formed on the first supporting portion so as to be disposed closer to the sensor wire than the sensor electrode pad; and a heater electrode pad connected to the heating wire and formed on the second supporting portion and the bridge portion.

Also, it is characterized in that the anti-etching dam is formed in the outer side of the heating wire.

And, it is characterized in that the heating wire comprises a plurality of arc portions formed in the shape of an arc, and a plurality of connecting portions connecting the arc portions.

Also, it is characterized in that the air gap is formed in multiple numbers in a discontinuous manner.

And, it is characterized in that the anti-etching dam is made of metal.

A micro sensor according to the present invention for achieving the above described objectives is characterized in that and comprises: a substrate comprising an anodic layer and having a first supporting portion; a first sensor electrode comprising a first sensor wire formed on the first supporting portion, and a first sensor electrode pad being connected to the first sensor wire; a second sensor electrode comprising a second sensor wire formed on the first supporting portion spaced apart from the first sensor electrode, and a second sensor electrode pad being connected to the second sensor wire; a heater electrode comprising a heating wire formed on the first supporting portion and formed surrounding at least a portion of the first sensor wire and the second sensor wire from the outer side thereof, and the first heater electrode pad and the second heater electrode pad connected to the both ends of the heating wires respectively and spaced apart from each other; a plurality of air gaps formed around the periphery of the first supporting portion in a discontinuous manner; and an anti-etching dam formed between the heating wire and the air gaps, wherein the heating wire comprises a plurality of arc portions formed in the shape of an arc, and a plurality of connecting portions connecting the arc portions, and the anti-etching dam is formed between the both ends of the heating wire in the shape of an arc.

A micro sensor according to the present invention for achieving the above described objectives is characterized in that and comprises: a substrate comprising an anodic layer and having a first supporting portion; a first sensor electrode comprising a first sensor wire formed on the first supporting portion, and a first sensor electrode pad being connected to the first sensor wire; a second sensor electrode comprising a second sensor wire formed on the first supporting portion spaced apart from the first sensor electrode, and a second sensor electrode pad being connected to the second sensor wire; a heater electrode comprising a heating wire formed on the first supporting portion and formed surrounding at least a portion of the first sensor wire and the second sensor wire from the outer side thereof, and the first heater electrode pad and the second heater electrode pad connected to the both ends of the heating wires respectively and spaced apart from each other; a plurality of air gaps formed around the periphery of the first supporting portion in a discontinuous manner; and an anti-etching dam formed between the heating wire and the air gaps, wherein the heating wire comprises: a plurality of straight line portions formed in the shape of a straight line and spaced apart from each other, and a plurality of curved portion connecting the straight line portions, and the anti-etching dam is formed between any one of the straight line portions located in the outer side thereof and the air gap.

Advantageous Effects of Invention

There are following effects according to the present invention.

The temperature uniformity is enhanced since the first supporting portion supporting the heater electrode can maintain its initial shape.

Also, the first supporting portion can be prevented from being damaged by not maintaining its initial shape thereof due to the anti-etching dam.

And, the heat capacity of the substrate is small since it is formed to be porous.

Also, the temperature uniformity of the heating wire is enhanced since it is formed to be the shape of a circle in general by including a plurality of arc portions and a plurality of connecting portions.

And, the location of the bridge portion can be designed freely by forming an anti-etching dam in a space between the first arc portion and the third arc portion.

Also, according to the present invention, it is suitable for mobile application owing to the low power consumption.

DETAILED DESCRIPTION OF EMBODIMENTS

Figure 1:
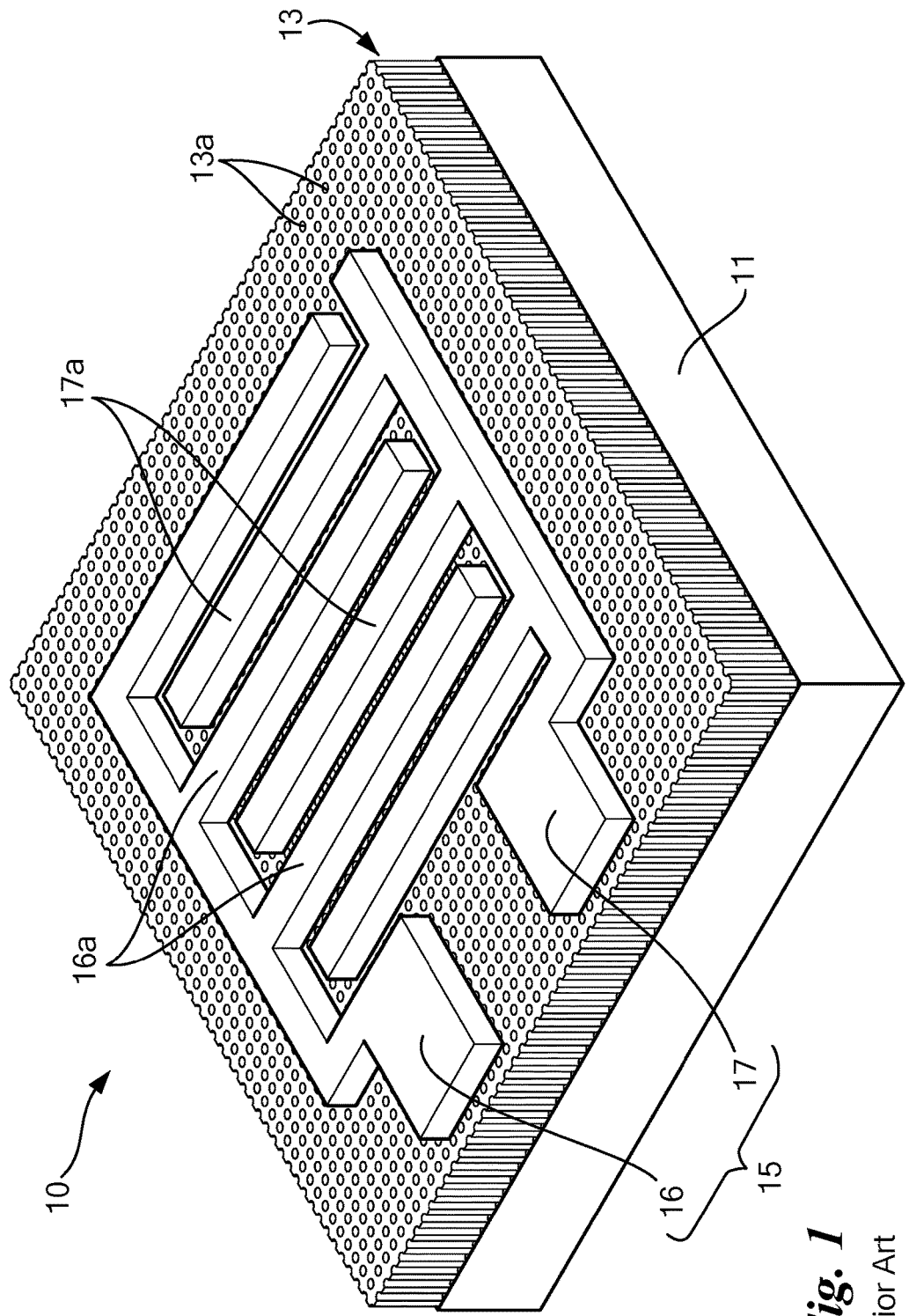
FIG. 1 is a perspective view illustrating a moisture sensor of the prior art.

Hereinafter, a preferred embodiment of the present invention will be described in detail with reference to the accompanying drawings. Advantages and features of the present invention and methods of accomplishing the same may be understood more readily by reference to the following detailed description of exemplary embodiments and the accompanying drawings. However, the present invention will be embodied in many different forms and is not limited to the embodiments set forth herein. Rather, these embodiments disclosed herein are provided also to complete the disclosure of the present invention and fully convey the concept of the invention to those skilled in the art, but the present invention will only be defined by the appended claims. The same reference numerals throughout the specification refer to like elements.

On the other hand, as used herein, the terms are intended to illustrate the embodiments and not intended to limit the invention. As used herein the singular includes the plural unless otherwise specified in the text. The expression 'comprises' and/or 'comprising' as used herein does not exclude mentioned components, steps, operation and/or the presence or addition of more than one different components, steps, operation and/or elements. In addition, since it is in accordance with the preferred exemplary embodiments, the reference symbols suggested according to the order of the description are not necessarily limited to that order.

The exemplary embodiments disclosed herein will now be described with reference to the accompanying drawings of cross-sectional views and/or plan views which are ideal exemplary drawings of the present invention. In the drawings, the thicknesses of the thin films and the sections are exaggerated for the effective description of the technical contents. Therefore, the exemplary drawings may be changed according to the manufacturing technologies and/or the tolerances and the like. In other words, the exemplary embodiments of the present invention are not limited to the specific configurations as illustrated herein, but the changes in the configurations being generated in accordance with the manufacturing processes are also included therein. Therefore, the exemplary sections specified in the drawings have approximate properties, and the shapes of the exemplary sections in the drawings are merely to illustrate the specific aspects of the sections of the elements but not to limit the scopes of the invention.

Hereinafter, a preferred embodiment of the present invention will be described in detail with reference to the accompanying drawings.

In describing various exemplary embodiments, for the convenience's sake, same names and same reference numerals will be assigned for the components performing same function even though exemplary embodiments are different from each other.

Also, configurations and operations already explained in the other exemplary embodiment will be omitted for the convenience's sake.

Figure 2:
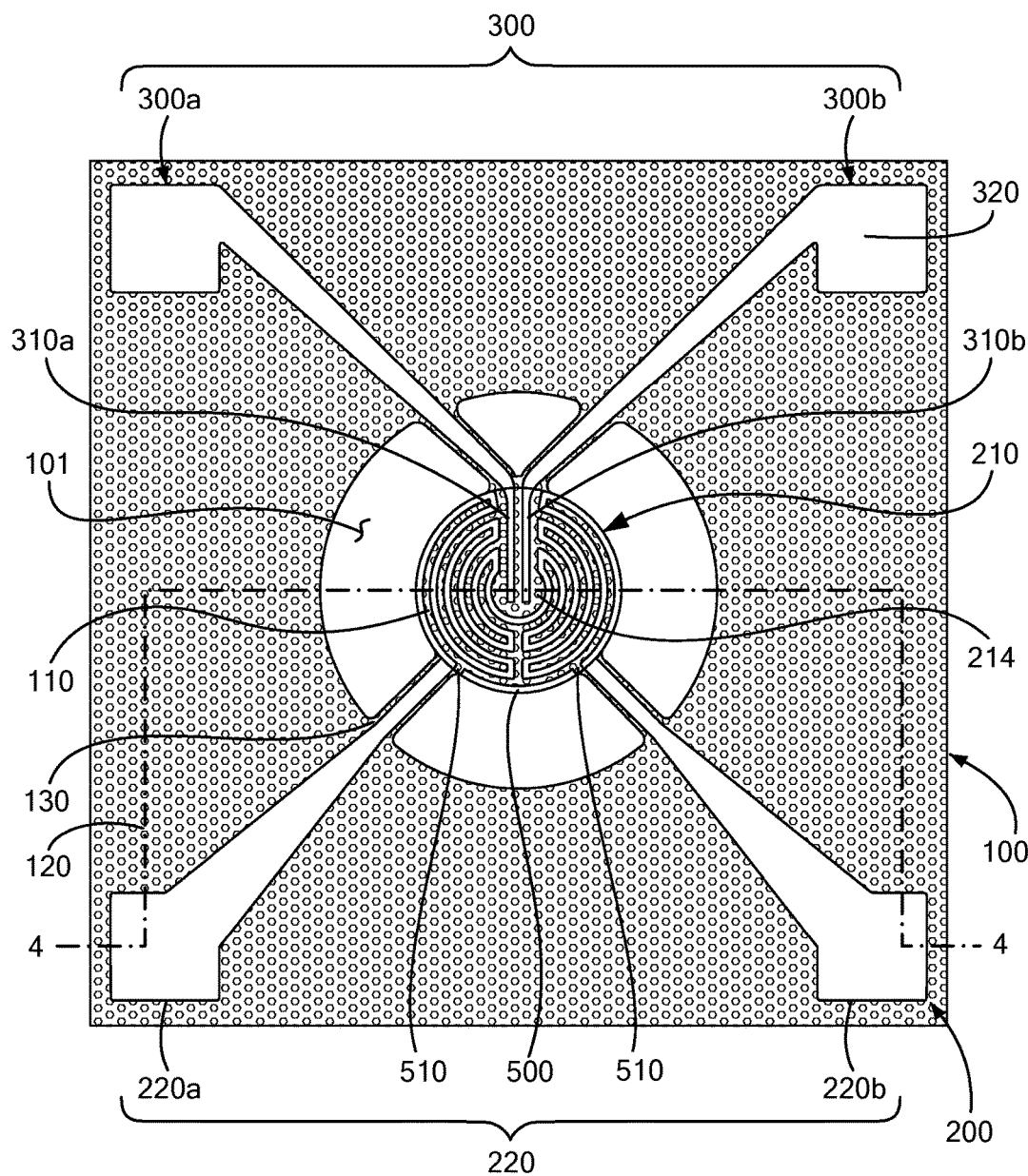
FIG. 2 is a plan view of a micro sensor provided with a micro heater according to a preferred first exemplary embodiment of the present invention (with sensing material omitted).
Figure 3:
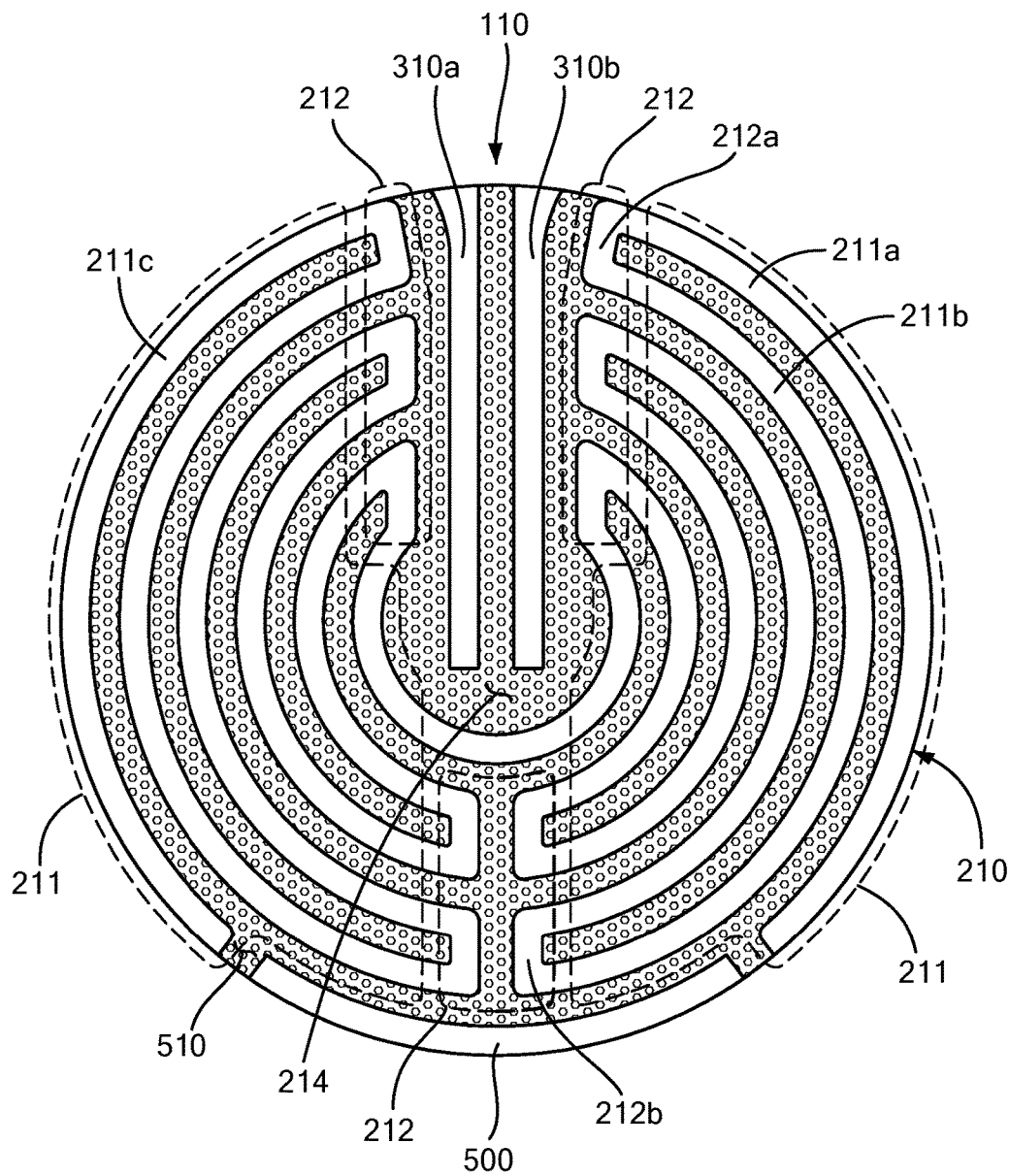
FIG. 3 is an exploded plan view of a first supporting portion (with sensing material omitted).
Figure 4:
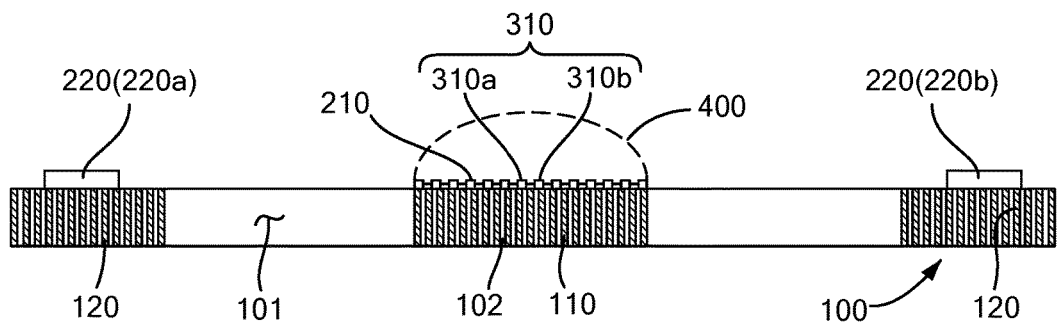
FIG. 4 is a cross-sectional view along the line 4-4 in FIG. 2.

For reference, the configurations of the present invention having same configurations of the prior arts, which will be described hereinafter, will be referred to the previously described prior arts, and separate detailed descriptions thereof will be omitted As illustrated in FIGS. 2 to 4, a micro sensor provided with a micro heater according to the first preferred exemplary embodiment of the present invention is characterized in that and comprises: a substrate 100 having a first supporting portion 110; a sensor electrode 300 formed on the substrate 100; an anti-etching dam 500 formed on the first supporting portion 110; and an air gap 101 formed in the periphery of the first supporting portion 110.

As the base material of a metallic substance is being anodized, an anodized layer comprising: a porous layer having a plurality of pores in the surface thereof; and a barrier layer existing beneath the porous layer, is formed. In here, the base material of a metallic substance may be aluminum (Al), titanium (Ti), tungsten (W), zinc (Zn), and the like; however, preferably, it is aluminum or an aluminum alloy which is light, easy to process, an excellent heat conductor, and free of heavy metal contamination.

As an example, by performing an anodizing treatment on the surface of aluminum, an anodized aluminum oxide layer comprising: a porous aluminum oxide layer having a plurality of pores 102 in the surface thereof; and a barrier layer existing beneath the porous aluminum oxide layer, is formed. The substrate 100 in the preferred exemplary embodiment of the present invention, for an example, may comprise only an aluminum oxide layer wherein aluminum is removed. Also, an electrode may be formed on the porous aluminum oxide layer of the aluminum oxide layer, and on the contrary, the electrode may be formed on the barrier layer. Also, it may comprise only a porous aluminum oxide layer wherein pores 102 are vertically penetrating by removing the barrier layer of the aluminum oxide layer.

Hereinafter, it will be described with reference to the substrate 100 wherein both the aluminum and the barrier layer are removed.

In the anodized aluminum, the aluminum and the barrier layer are removed so that the pores 102 of the substrate 100 are penetrating along the vertical direction. Since the substrate is formed with a porous aluminum oxide layer the heat capacity of the micro heater becomes small.

The substrate 100 comprises: a first supporting portion 110 formed in the center of the substrate 100 to be the shape of a cylinder; and a second supporting portion 120 formed in the outer side spaced apart from the first supporting portion 110; and a bridge portion 130 connecting the first supporting portion 110 and the second supporting portion 120. Also, a plurality of air gaps 101 are formed in the periphery of the first supporting portion 110, that is, between the first supporting portion 110 and the second supporting portion 120.

The first supporting portion 110 is located in the center of the substrate 100, and has the shape of a cylinder in overall, and a plurality of bridge portions 130 are connected in the outer circumference thereof.

Also, a plurality of air gaps 101 are formed in the outer circumference of the first supporting portion 110. A plurality of air gaps 101 may be formed discontinuously. The air gaps 101 and the bridge portions 130 are alternately disposed around the periphery of the first supporting portion 110. Such bridge portions are formed by forming the air gaps 101 in a discontinuous manner through the etching of the periphery of the first supporting portion 110. Thus, the one ends of the plurality of the bridge portions 130 are connected to the first supporting portion 110, and the other ends are connected to the second supporting portion 120.

The sensor electrode 300, the heater electrode 200, and the anti-etching dam 500 which are formed on the upper surface of the substrate 100 will be described hereinbelow.

The sensor electrode 300 is formed on the upper surface of the substrate.

Such sensor electrode 300 detects the change in the electrical characteristics when a gas is absorbed in the sensing material.

The sensor electrode 300 comprises a first sensor electrode 300a and a second sensor electrode 300b disposed apart from the first sensor electrode 300a. The first sensor electrode 300a and the second sensor electrode 300b are disposed spaced apart along the left-right direction, and formed symmetrically with respect to the center line vertically disposed in the plan view.

The sensor electrodes 300a and 300b respectively comprise sensor wires 310a and 310b formed on the first supporting portion 110, and a sensor electrode pad 320 respectively connected to the sensor wires 310a and 310b and respectively formed in the bridge portions 130 and the second supporting portion 120.

The first sensor electrode 300a comprises the first sensor wire 310a and the first sensor electrode pad connected to the first sensor wire 310a. The second sensor electrode 300b comprises the second sensor wire 310b and the second sensor electrode pad connected to the second sensor wire 310b. The sensor wires 310a and 310b comprise the first sensor wire 310a and the second sensor wire 310b. The sensor electrode pad 320 comprises the first sensor electrode pad and the second sensor electrode pad. The sensor wires 310a and 310b are disposed on the upper surface of the first supporting portion 110. The widths of the sensor wires 310a and 310b are formed to have a constant width. The sensor electrode pad 320 is respectively located in the bridge portions 130 and the second supporting portion 120, and formed to have a wider width than those of the first sensor wire 310a and the second sensor wire 310b. The sensor electrode pad 320 of the first sensor electrode 300a and the second sensor electrode 300b are respectively disposed in the two neighboring corners of the substrate 100 being formed to have a rectangular shape, and formed in a way that the width thereof becomes wider as it travels towards the end portion. In other words, the sensor electrode pad 320 is formed in a way that the width thereof becomes narrower as it travel towards the first sensor wire 310a and the second sensor wire 310b.

The sensor electrodes 300 comprise one of or composite material including at least one of Pt, W, Co, Ni, Au, and Cu.

The heater electrodes 200 are formed on the upper surface of the substrate 100.

When the electrode is formed on the porous aluminum oxide layer of the aluminum oxide layer, the upper side of the pores 102 located beneath the heater electrode 200 and the sensor electrode 300 is blocked by the heater electrode 200 and the sensor electrode 300, and the lower side is blocked as well. Unlike this, when the electrode is formed on the barrier layer of the aluminum oxide layer, the upper side of the pores 102 located beneath the heater electrode 200 and the sensor electrode 300 is blocked, but the lower side is open. Unlike this, when the barrier layer of the aluminum oxide layer is removed, the upper side of the pores 102 located beneath the heater electrode 200 and the sensor electrode 300 is blocked by the heater electrode 200 and the sensor electrode 300, but the lower side is open. In this way, since the heater electrode 200 is formed on the porous aluminum oxide layer, the micro sensor has a small heat capacity.

The heater electrode 200 comprises: a heater wire 210 formed on the first supporting portion 110 so as to be disposed nearer to the sensor wires 310a and 310b than the sensor electrode pad 320; and a heater electrode pad 220 connected to the heating wire 210 and formed on the second supporting portion 120 and the bridge portions 130.

The heating wire 210 is formed on the first supporting portion 110, and formed surrounding at least a portion of the first sensor wire 310a and the second sensor wire 310b. And, the heater electrode pad 220 is respectively connected to the both end portions of the heating wire 210; and comprises the first heater electrode pad 220a and the second heater electrode pad 220b, which are spaced apart from each other. The heating wire 210 is disposed on the upper surface of the first supporting portion 110 of the substrate 100.

When viewed from the plan view as shown in FIG. 3, the heating wire 210 is symmetrically formed with respect to the vertical center line of the first supporting portion 110, and comprises a plurality of arc portions 211, formed to be in the shape of an arc, and a plurality of connecting portions 212a and 212b connecting the arc portions 211a, 211b and 211c.

The heating wire 210 is comprised of repeatedly and alternately connected a plurality of arc portions 211 and a plurality of connecting portions 212 respectively, wherein: a first arc portion 211a, formed in the shape of an arc and disposed close to the air gap 101, is connected to; a first connecting portion 212a, bended and extended from the one end portion of the first arc portion 211a towards the inner side of the first supporting portion 110, and this is connected to; a second arc portion 211b, formed in the shape of an arc at the end portion of the first connecting portion 212a and extended and disposed towards the inner side of the first arc portion 211a, and this is connected to; a second connecting portion 212b formed at the end portion of the second arc portion 211b and extended towards the inner side of the first supporting portion 110, and so on.

The heating wire 210 is connected from the first arc portion 211a to the third arc portion 211c and forms an integral body, and becomes symmetrical with respect to the center line of the first supporting portion 110.

As shown in FIG. 2, the plurality of arc portions 211 of the heating wire 210 is formed in the shape of an approximate half circle arc and to be symmetrical in the left-right direction, thereby forming an approximate circle. Owing to this, the temperature uniformity of the first supporting portion 110 is enhanced.

The center area of the heating wire 210 is a place where the arc portions 211 of the left and the right sides meet, wherein the two arc portions 211 having the shape of an arc are joined together and form a circular shape whose upper side is open. And, in the inner side thereof, a separation space portion 214 is formed. The separation space portion 214 is formed from the center area of the heating wire 210 and extended up to the upper portion of the heating wire 210. That is, the heating wire 210 is laterally spaced apart from the upper center area down to the center area so that the separation space portion 214 is formed. The sensor wires 310a and 310b are disposed in the separation space portion 214. That is, the heating wire 210 is formed so as to surround at least a portion of the first sensor wire 310a and the second sensor wire 310b at the outer sides of the sensor wires. Also, the second heater electrode pad 220b is connected to the other end portion of the first arc portion 211a, and the first heater electrode pad 220a is connected to the one end portion of a third arc portion 211c.

The heater electrodes 200 comprise one of or composite material including at least one of Pt, W, Co, Ni, Au, and Cu.

Meanwhile, an anti-etching dam 500 is formed between the end portions of the first arc portion 211a and the third arc portion 211c where the first heater electrode pad 220a and the second heater electrode pad 220b are respectively connected.

The anti-etching dam 500 is disposed in the shape of an arc between the heater electrodes 200, in other words, between the heating wire 210 and the air gap 101. The anti-etching dam 500 is formed spaced apart from the neighboring heating wire 210.

The anti-etching dam 500 is preferably made of a metal. The material of the anti-etching dam 500 may be the same as the electrode material, and the material of the electrode herein may be a metal such as Pt, Al, Cu, and the like.

As illustrated in FIG. 3, the first arc portion 211a and the third arc portion 211c are formed to have a length shorter than those of the remaining arc portions 211. In the outer circumference of the heating wire 210, a space 510 is formed between the end portions of the first arc portion 211a and the third arc portion 211c, and the anti-etching dam 500 is located in this space 510.

The space 510 of the circumferential area of the heating wire 210 is partially filled as much as the area wherein the anti-etching dam 500 is formed. Due to this, when viewed from plan view, the outer circumference of the heating wire 210 and the anti-etching dam 500 is formed to be a circular shape; therefore, it is suitable for a mobile application since the gases to be measured can be quickly and accurately detected even with low power consumption.

Also, by forming the anti-etching dam 500 in the space 510 between the first arc portion 211a and the third arc portion 211c, the bridge portion 130 can be designed in a way that the structure of the substrate 100 becomes more stable. The end portions of the first arc portion 211a and the third arc portion 211c are respectively located so as to be close to the end portions of the two bridge portions 130 whereon the heater electrode pad 220 is respectively formed, and then a circular shaped heating wire 210 is formed on the upper surface of the first supporting portion 110. And, the anti-etching dam 500 is formed in the space 510 between the neighboring end portions of the first arc portion 211a and the third arc portion 211c. The anti-etching dam 500 can be formed corresponding to the size of the space 510 between the first arc portion 211a and the third arc portion 211c. Thus, since the anti-etching dam 500 is formed in the space 510 between the heating wire 210 and the first arc portion 211a and the third arc portion 211c regardless of the location of the bridge portion 130. Owing to this, the location of the bridge portion 130 connecting the first supporting portion 110 and the second supporting portion 120 can be freely designed considering the stability and the like of the overall sensor structure.

The anti-etching dam 500 prevents a portion of the space 510 of the first supporting portion 110 from being damaged by the etching solution when the air gap 101 is formed through etching. In other words, the anti-etching dam 500 is formed close to the heating wire 210 formed on the first supporting portion 110 so that the regular shape (for example, original shape) of the first supporting portion 110 supporting the heating wire 210 is prevented from being damaged. Through maintaining of the regular shape (for example, original shape) of the first supporting portion 110, the temperature uniformity of the first supporting portion 110 is enhanced, therefore, the temperature distribution of the heating wire 210 on the first supporting portion 110 whose temperature is elevated with a low power becomes more uniform.

The heater electrode pad 220 comprises the first heater electrode pad 220a and the second heater electrode pad 220b being respectively connected to the both end portions of the heating wire 210. In this way, the heater electrode pad 220 comprises at least two each. The heater electrode pad 220 is disposed at the remaining two neighboring corners of the substrate 100, and formed in a way that the width thereof is getting wider as it travels towards the outer side. In other words, the heater electrode pad 320 is formed in a way that the width thereof becomes narrower as it travels towards the heating wire 210. The heater electrode pad 220 is formed to have a width wider than the heating wire 210.

Meanwhile, in the first supporting portion 110, a dummy electrode comprising metal and being formed spaced apart from the heater electrode 200 may further be formed.

A discoloration protection layer (not shown) is formed on the entire upper surface of the heater electrode 200 and the sensor electrode 300. The discoloration protection layer may be formed of an oxide series material. Further, the discoloration protection layer is formed of at least one of tantalum oxide ($TaO_x$), titanium oxide ($TiO_2$), silicon oxide ($SiO_2$), and aluminum oxide ($Al_2O_3$).

And, a soldering metal is formed at the end portions of the heater electrode pad 220 and the sensor electrode pad 320. The soldering metal is formed on the upper side of the discoloration protection layer. The soldering metal may be at least one of Au, Ag, and Sn.

An air gap 101 is formed in the substrate 100 so as to surround the heating wire 210 and the sensor wires 310a and 310b. The air gap 101 is disposed in the circumference of the first supporting portion 110, that is, in the circumference of the heating wire 210 and the sensor wires 310a and 310b.

The maximum width (lateral width) of the air gap 101 is formed to be wider than the maximum width of the pore 102. The air gap 101 is formed to be the shape of an arc, and 4 each are formed. A plurality of air gaps 101 is disposed spaced apart towards the circumferential direction. That is, the air gaps 101 are formed in multiple numbers discontinuously.

More in detail, the air gap 101 is disposed: between the sensor electrode pad 320 of the first sensor electrode 300a and the first heater electrode pad 220a; between the heater electrode pad 220a and the second heater electrode pad 220b; between the second heater electrode pad 220b and the sensor electrode pad 320 of the second sensor electrode 300b; and between the sensor electrode pad 320 of the second sensor electrode 300b and the sensor electrode pad 320 of the first sensor electrode 300a. That is, the air gap 101 is formed in the area excluding the area which supports heater electrode 200 and the sensor electrode 300.

The air gap 101 is formed penetrating through along the up-down direction. That is, the air gap 101 is a space formed penetrating through from the upper surface of the substrate 100 down to the bottom surface thereof.

Due to this air gap 101, the first supporting portion 110 which commonly supports the heating wire 210 and the sensor wires 310a and 310b, the second supporting portion 120 which supports the heater electrode pad 220 and the sensor electrode pad 320, and the bridge portion 130 are formed on the substrate 100. That is, the air gap 101 is formed between the first supporting portion 110 and the second supporting portion 120. Thus, the air gap 101 and the bridge portion 130 are alternately disposed around the periphery of the first supporting portion 110.

The first supporting portion 110 is formed in the shape of a circle when viewed from the plan view as shown in FIG. 2, and surrounded by the air gap. The first supporting portion 110 is formed to be larger than the area of the heating wire 210 and the sensor wires 310a and 310b.

The first supporting portion 110 and the second supporting portion 120 are connected to each other through the bridge portion 130.

And, the first supporting portion 110 and the second supporting portion 120 are spaced apart from each other due to the air gap 101 except the bridge portion 130. Therefore, the first supporting portion 110 and the second supporting portion 120 are connected to each other at four points through the four bridge portions 130 as illustrated in FIG. 2.

In the first supporting portion 110, a sensing material 400 covering the heating wire 210 and the sensor wires 310a and 310b is formed. That is, the sensing material 400 is formed in the location corresponding to the first supporting portion 110. The sensing material 400 is formed by printing. In this way, when the sensing material 400 is formed by printing, a trace having the shape of a mesh net is left on the sensing material 400 after the sensing material 400 is formed.

Figure 5:
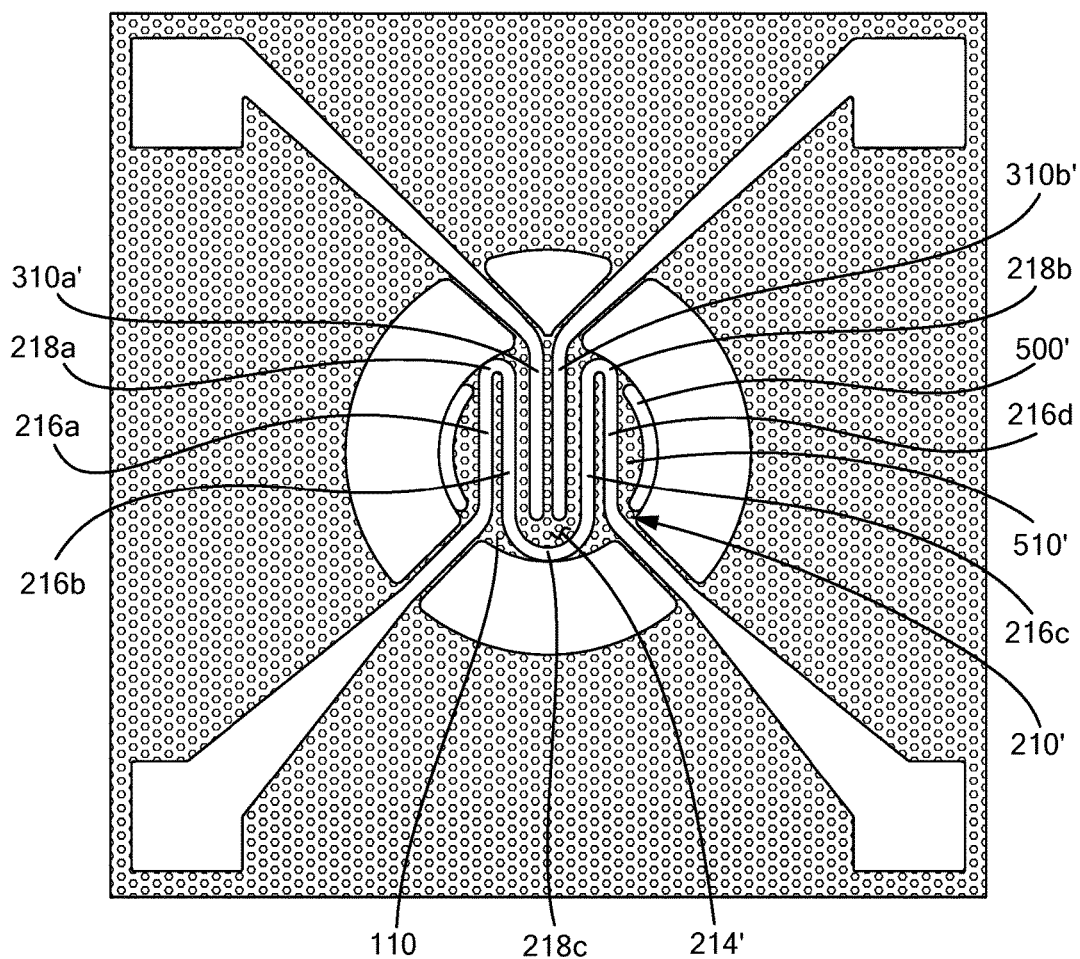
FIG. 5 is a plan view of a micro sensor provided with a micro heater according to a preferred second exemplary embodiment of the present invention (with sensing material omitted).

Hereinafter, a micro sensor provided with a micro heater according to the second preferred exemplary embodiment of the present invention will be described with reference to FIG. 5. Hereinafter, only a heating wire 210' and an anti-etching protection dam 500', which are different than those of the first exemplary embodiment, will be described.

When viewed from the plan view, the heating portion 210' is formed on the first supporting portion 110 to be the shape of a straight line, and comprises a plurality of straight portions 216 spaced apart from each other, and a plurality of curved line portions 218 connecting the straight line portions 216. In the straight line portions 216, a first straight line portion 216a and a second straight line portion 216b which are disposed close to each other but spaced apart from each other, and the first curved line portion 218a, connecting the first straight line portion 216a and the second straight line portion 216b, are connected to each other to form a '∩' shape when viewed in the plan view.

A third straight line portion 216c and a fourth straight line portion 216d which are disposed close to each other but spaced apart from each other, and a second curved line portion 218b, connecting the third straight line portion 216c and a fourth straight line portion 216d, are connected to each other to form a '∩' shape when viewed in the plan view.

And, the third curved line portion 218c connecting the second straight line portion 216b and the third straight line portion 216c forms a 'U' shape when viewed in the plan view, and disposed between the two '∩' shapes.

A separation space portion 214' is formed between the second straight line portion 216b and the third straight line portion 216c which are spaced apart from each other.

A first sensor line 310a and a second sensor line 310b are disposed in the separation space portion 214'.

And, an anti-etching dam 500' is formed between any one of the straight line portions 216 located in the outer side thereof and the air gap 101.

The anti-etching dam 500' can be formed in the shape of an arc between the first straight line portion 216a and its neighboring air gap 101, and between the fourth straight line portion 216d and its neighboring air gap 101.

Owing to this, the space 510' is prevented from damages during the etching process for forming the air gap 101. That is, the first supporting portion 110 maintains its original shape, and the temperature uniformity is enhanced thereby. Hereinafter, the operation of the exemplary embodiment having the aforementioned configuration will be described.

In order to measure the gas concentration, first, a constant power is applied to the two of the heater electrode pads 220 of the heater electrode 200, and the sensing material 400 being contacted thereto and located in the center of the sensor is heated to a constant temperature.

At this state, when the gases existing around (the sensing material) are being absorbed by or desorpted from the sensing material 400 in accordance with the concentration of the gases, the changes occurring in the characteristics of the sensing material 400 is measured through quantification of the electrical conductivity of the sensing material 400 using the measured potential difference between the sensor electrode pads 320 by involving (using) an external circuit which is electrically connected to the sensing material 400.

Also, for more accurate measurement, concentration of the interested gas is measured after restoring the sensing material 400 to its initial state by forcibly removing the other gas species or moisture already absorbed in the sensing material 400 through heating thereof to a high temperature using the heater electrode 200.

As described above, although it is described with reference to the preferred exemplary embodiments of the present invention, an ordinary person skilled in the art will appreciate that various modifications and alterations of the present invention are possible without departing from the spirit and scope of the invention.

DESCRIPTION OF SYMBOLS

100: substrate
101: air gap
102: pore
110: first supporting portion
120: second supporting portion
130: bridge portion
200: heater electrode
210,210': heating wire
211: arc portion
211a: first arc portion
211b: second arc portion
211c: third arc portion
212: connecting portion
212a: first connecting portion
212b: second connecting portion
214,214': separation space portion
216: straight line portion
216a: first straight line portion
216b: second straight line portion
216c: third straight line portion
216d: fourth straight line portion
218: curved line portion
218a: first curved line portion
218b: second curved line portion
218c: third curved line portion
220: heater electrode pad
220a: first heater electrode pad
220b: second heater electrode pad
300: sensor electrode
300a: first sensor electrode
300b: second sensor electrode
310a, 310a': first sensor wire
310b, 310b': second sensor wire
320: sensor electrode pad
400: sensing material 500, 500': anti-etching dam
510, 510': space

What is claimed is:

1. A micro heater comprising:
a substrate having a first supporting portion;
a heater electrode formed on said first supporting portion;
an anti-etching dam configured for preventing shape deformation of the first supporting portion by etching solution, formed on said first supporting portion; and
an air gap formed by etching and surrounding the periphery of said first supporting portion,
wherein the substrate further comprises a second supporting portion and a bridge portion connecting said first supporting portion and said second supporting portion, and said heater electrode comprises a heating wire formed on said first supporting portion and a heater electrode pad connected to said heating wire and formed on said second supporting portion and said bridged portion,
wherein the heating wire comprises a plurality of arc portions formed in the shape of an arc, and a plurality of connecting portions connecting said arc portions,
wherein the anti-etching dam is formed between one end of the outermost arcs of the plurality of arc portions forming the heating wire and the other end of the outermost arcs.

2. The micro heater according to claim 1,
characterized in that said anti-etching dam is disposed between said heater electrode and said air gap.

3. The micro heater according to claim 1,
characterized in that said substrate is an anodized layer wherein a metallic base material is removed after anodizing thereof.

4. The micro heater according to claim 1,
characterized in that said air gap is a space formed penetrating from the upper surface of said substrate down towards the bottom surface thereof.

5. The micro heater according to claim 1,
characterized in that said air gap is formed in multiple numbers in a discontinuous manner.

6. The micro heater according to claim 1,
characterized in that said anti-etching dam is made of metal.

7. A micro sensor comprising:
a substrate having a first supporting portion;
a sensor electrode formed on said first supporting portion;
a heater electrode formed on said first supporting portion;
an anti-etching dam configured for preventing shape deformation of the first supporting portion by etching solution, formed on said first supporting portion; and
an air gap formed by etching and surrounding the periphery of said first supporting portion,
wherein the substrate further comprises a second supporting portion and a bridge portion connecting said first supporting portion and said second supporting portion, and said heater electrode comprises a heating wire formed on said first supporting portion and a heater electrode pad connected to said heating wire and formed on said second supporting portion and said bridged portion,
wherein the heating wire comprises a plurality of arc portions formed in the shape of an arc, and a plurality of connecting portions connecting said arc portions,
wherein the anti-etching dam is formed between one end of the outermost arcs of the plurality of arc portions forming the heating wire and the other end of the outermost arcs.

8. The micro sensor according to claim 7,
characterized in that said anti-etching dam is disposed between said heater electrode and said air gap.

9. The micro sensor according to claim 7,
characterized in that said substrate is an anodized layer wherein a metallic base material is removed after anodizing thereof.

10. The micro sensor according to claim 7,
characterized in that said air gap is a space formed penetrating from the upper surface of said substrate down towards the bottom surface thereof.

11. The micro sensor according to claim 7,
characterized in that said air gap is formed in multiple numbers in a discontinuous manner.

12. The micro sensor according to claim 7,
characterized in that said anti-etching dam is made of metal.

13. A micro sensor comprising:
a substrate comprising an anodic layer and having a first supporting portion;
a first sensor electrode comprising a first sensor wire formed on said first supporting portion, and a first sensor electrode pad being connected to said first sensor wire;
a second sensor electrode comprising a second sensor wire formed on said first supporting portion spaced apart from said first sensor electrode, and a second sensor electrode pad being connected to said second sensor wire;
a heater electrode comprising a heating wire formed on said first supporting portion and formed surrounding at least a portion of said first sensor wire and said second sensor wire from the outer side thereof, and a first heater electrode pad and a second heater electrode pad connected to the both ends of the heating wire respectively and spaced apart from each other;
a plurality of air gaps formed by etching and surrounding the periphery of said first supporting portion in a discontinuous manner; and
an anti-etching dam configured for preventing shape deformation of the first supporting portion by etching solution, formed between said heating wire and said air gaps, wherein said heating wire comprises a plurality of arc portions formed in the shape of an arc, and a plurality of connecting portions connecting said arc portions, and said anti-etching dam is formed between the both ends of said heating wire in the shape of an arc.

* * * * *